United States Patent
Austria

(10) Patent No.: US 10,292,729 B2
(45) Date of Patent: *May 21, 2019

(54) SIDE ACTIVATED SAFETY SCALPEL FOR LEFT AND RIGHT HAND USERS WITH BLADE REMOVAL SYSTEM

(71) Applicant: Aspen Surgical Products, Inc., Caledonia, MI (US)

(72) Inventor: Georgene Austria, West Hills, CA (US)

(73) Assignee: Aspen Surgical Products, Inc., Caledonia, MI (US)

( * ) Notice: Subject to any disclaimer, the term of this patent is extended or adjusted under 35 U.S.C. 154(b) by 79 days.

This patent is subject to a terminal disclaimer.

(21) Appl. No.: 15/455,804

(22) Filed: Mar. 10, 2017

(65) Prior Publication Data

US 2017/0181763 A1 Jun. 29, 2017

Related U.S. Application Data

(63) Continuation of application No. 13/802,522, filed on Mar. 13, 2013, now Pat. No. 9,622,773.

(Continued)

(51) Int. Cl.
*A61B 17/3211* (2006.01)
*A61B 17/3213* (2006.01)
*A61B 17/3217* (2006.01)

(52) U.S. Cl.
CPC ...... *A61B 17/3211* (2013.01); *A61B 17/3213* (2013.01); *A61B 17/3217* (2013.01); *A61B 2017/32113* (2013.01)

(58) Field of Classification Search
None
See application file for complete search history.

(56) References Cited

U.S. PATENT DOCUMENTS

| D334,981 S | 1/1886 | Rampe, Jr. |
| 1,002,468 A | 9/1911 | Strangman |

(Continued)

FOREIGN PATENT DOCUMENTS

| AU | 620691 B2 | 2/1992 |
| GB | 846877 A | 8/1960 |

(Continued)

OTHER PUBLICATIONS

QlickSmart of Australia, Blade Flask Blade Remover and Blade Cassette, QlickSmart Product Literature, http://qlicksmart.com/English/Home.htm, date unknown, 3 pages.

(Continued)

*Primary Examiner* — Hwei-siu C Payer
(74) *Attorney, Agent, or Firm* — Price Heneveld LLP

(57) ABSTRACT

A surgical scalpel is presented which combines the attributes of cost-effectiveness in design while being ambidextrous and autoclavable. The design of the device affords left handed or right handed medical personnel with the feel, weight and balance of the original metal unguarded scalpel, while maintaining safety through the shielding of the blade during non-use and the ability to dispose of the blade in a safe controlled manner without having to place one's hands near the unguarded sharp. Surgeons of either dexterity are able to learn and operate using similar techniques and instruments heretofore not available to them. No longer must a left handed surgeon be forced into the right handed world to perform surgery. The device is designed to use existing styles of blades currently available without needing costly inventories of specially created blades for the multitude of other such devices on the market.

20 Claims, 7 Drawing Sheets

Related U.S. Application Data

(60) Provisional application No. 61/685,480, filed on Mar. 19, 2012.

(56) References Cited

U.S. PATENT DOCUMENTS

| | | |
|---|---|---|
| D194,087 S | 11/1962 | Jenkins |
| D194,418 S | 1/1963 | Gaspar |
| 3,380,573 A | 4/1968 | Gulotta |
| 3,442,378 A | 5/1969 | Wolfe |
| 3,696,920 A | 10/1972 | Lahay |
| 3,785,544 A | 1/1974 | Smith |
| D231,714 S | 5/1974 | Arthur |
| 3,916,448 A | 11/1975 | Hamel |
| 3,921,289 A | 11/1975 | Hasegawa |
| D248,871 S | 8/1978 | Forsman et al. |
| 4,106,620 A | 8/1978 | Brimmer et al. |
| D249,362 S | 9/1978 | Forsman et al. |
| 4,120,397 A | 10/1978 | Neumann |
| 4,168,777 A | 9/1979 | Gaskell et al. |
| 4,173,071 A | 11/1979 | Ishida |
| 4,180,162 A | 12/1979 | Magney |
| 4,270,416 A | 6/1981 | Thompson |
| 4,318,473 A | 3/1982 | Sandel |
| 4,386,457 A | 6/1983 | Coombs |
| 4,395,807 A | 8/1983 | Eldridge, Jr. et al. |
| D273,615 S | 4/1984 | Maskrey |
| 4,466,539 A | 8/1984 | Frauenhoffer |
| D275,833 S | 10/1984 | Malpass |
| D276,462 S | 11/1984 | Villarreal |
| 4,730,376 A | 3/1988 | Yamada |
| 4,746,016 A | 5/1988 | Pollak et al. |
| 4,903,390 A | 2/1990 | Vidal et al. |
| 4,930,234 A | 6/1990 | Schmidt |
| 4,971,271 A | 11/1990 | Sularz |
| 4,998,334 A | 3/1991 | Pemberton et al. |
| 5,024,326 A | 6/1991 | Sandel et al. |
| 5,036,866 A | 8/1991 | Eldridge, Jr. et al. |
| D319,873 S | 9/1991 | Rouse |
| 5,071,426 A | 12/1991 | Dolgin et al. |
| 5,088,173 A | 2/1992 | Kromer et al. |
| D327,743 S | 7/1992 | Frenkel et al. |
| D328,026 S | 7/1992 | Stenstrom |
| 5,163,553 A | 11/1992 | Cantwell et al. |
| 5,193,678 A | 3/1993 | Janocik et al. |
| D334,973 S | 4/1993 | Valentine et al. |
| 5,207,696 A | 5/1993 | Matwijcow |
| D337,830 S | 7/1993 | Coyne et al. |
| D341,883 S | 11/1993 | Jones et al. |
| D343,687 S | 1/1994 | Houghton et al. |
| 5,275,606 A | 1/1994 | Abidin et al. |
| 5,299,357 A | 4/1994 | Wonderley et al. |
| 5,312,429 A | 5/1994 | Noack |
| 5,330,492 A | 7/1994 | Haugen |
| 5,330,494 A | 7/1994 | Van Der Westhuizen et al. |
| D349,204 S | 8/1994 | Lefebvre |
| 5,346,677 A | 9/1994 | Risk |
| 5,361,902 A | 11/1994 | Abidin et al. |
| 5,363,958 A | 11/1994 | Horan |
| 5,370,654 A | 12/1994 | Abidin et al. |
| D355,513 S | 2/1995 | Posenauer |
| 5,417,704 A | 5/1995 | Wonderley |
| 5,431,672 A | 7/1995 | Cote et al. |
| 5,433,321 A | 7/1995 | Abidin et al. |
| 5,449,068 A | 9/1995 | Gharibian |
| D366,527 S | 1/1996 | Paterson |
| 5,482,067 A | 1/1996 | Wittrock et al. |
| D369,295 S | 4/1996 | Kobari et al. |
| 5,527,329 A | 6/1996 | Gharibian |
| D372,782 S | 8/1996 | Spehalski |
| D374,282 S | 10/1996 | Hoftman |
| 5,569,281 A | 10/1996 | Abidin et al. |
| 5,571,127 A | 11/1996 | Decampli |
| D376,647 S | 12/1996 | Marsh et al. |
| 5,378,408 A | 3/1997 | Pyeatt et al. |
| 5,662,221 A | 9/1997 | Abidin et al. |
| 5,662,669 A | 9/1997 | Abidin et al. |
| 5,667,067 A | 9/1997 | Gabriel |
| 5,683,407 A | 11/1997 | Jolly |
| D387,177 S | 12/1997 | Davis |
| 5,699,908 A | 12/1997 | Frye et al. |
| 5,706,942 A | 1/1998 | Vila et al. |
| 5,729,879 A | 3/1998 | Hoftman |
| 5,741,289 A | 4/1998 | Jolly et al. |
| 5,752,968 A | 5/1998 | Jolly et al. |
| 5,765,470 A | 6/1998 | Sitro |
| 5,791,472 A | 8/1998 | Davis |
| 5,792,162 A | 8/1998 | Jolly et al. |
| 5,827,309 A | 10/1998 | Jolly et al. |
| D402,767 S | 12/1998 | Davis et al. |
| 5,868,771 A | 2/1999 | Newman et al. |
| 5,875,532 A | 3/1999 | Musgrave et al. |
| 5,875,533 A | 3/1999 | Henry |
| 5,938,027 A | 8/1999 | Soroff et al. |
| 5,938,676 A | 8/1999 | Cohn et al. |
| 5,941,892 A | 8/1999 | Cohn et al. |
| 5,964,161 A | 10/1999 | Conway |
| 5,968,663 A | 10/1999 | Muggli |
| 6,212,803 B1 | 4/2001 | Key |
| 6,216,868 B1 | 4/2001 | Rastegar et al. |
| D441,192 S | 5/2001 | Park |
| 6,254,621 B1 | 7/2001 | Shackelford et al. |
| D449,685 S | 10/2001 | Morrison |
| D450,130 S | 11/2001 | Goldstein |
| D450,391 S | 11/2001 | Hunt et al. |
| 6,426,041 B1 | 7/2002 | Smith |
| 6,589,258 B2 | 7/2003 | Pilo et al. |
| D479,328 S | 9/2003 | Reynolds et al. |
| 6,626,925 B2 | 9/2003 | Newman et al. |
| D481,129 S | 10/2003 | DiCesare et al. |
| 6,629,985 B1 | 10/2003 | Kiehne |
| D482,788 S | 11/2003 | Montgomery et al. |
| 6,645,216 B2 | 11/2003 | Masury et al. |
| D483,123 S | 12/2003 | Montgomery et al. |
| D489,454 S | 5/2004 | Koseki |
| D490,153 S | 5/2004 | Montgomery et al. |
| 6,757,977 B2 | 7/2004 | Dambal et al. |
| D504,175 S | 4/2005 | Westbrook |
| 6,955,002 B2 | 10/2005 | Sandel et al. |
| 7,036,660 B1 | 5/2006 | Abidin et al. |
| 7,070,051 B2 | 7/2006 | Kanner et al. |
| D528,206 S | 9/2006 | Bierman |
| D535,026 S | 1/2007 | Griffin et al. |
| 7,155,795 B2 | 1/2007 | Abidin et al. |
| 7,156,231 B1 | 1/2007 | Austria |
| 7,159,713 B1 | 1/2007 | Austria |
| 7,172,611 B2 | 2/2007 | Harding et al. |
| 7,201,760 B2 | 4/2007 | Masury et al. |
| 7,207,999 B2 | 4/2007 | Griffin et al. |
| D542,415 S | 5/2007 | Sandel |
| D544,600 S | 6/2007 | Wentling |
| D549,327 S | 8/2007 | Aparici et al. |
| 7,303,568 B2 | 12/2007 | Jannot |
| D561,898 S | 2/2008 | Goto |
| 7,346,989 B2 | 3/2008 | Shi |
| D568,475 S | 5/2008 | Sandel et al. |
| D568,491 S | 5/2008 | Koseki |
| D568,492 S | 5/2008 | Koseki |
| D568,493 S | 5/2008 | Koseki |
| 7,398,880 B2 | 7/2008 | Henry |
| 7,441,655 B1 | 10/2008 | Hoftman |
| D583,821 S | 12/2008 | Richter |
| 7,458,177 B2 | 12/2008 | Sandel et al. |
| D596,311 S | 7/2009 | Antons |
| D608,015 S | 1/2010 | Sandel |
| D608,456 S | 1/2010 | Sandel |
| D612,050 S | 3/2010 | Baynham |
| D616,089 S | 5/2010 | Van der Stappen |
| 7,713,280 B2 | 5/2010 | Marshall et al. |
| D618,821 S | 6/2010 | Larsen |
| D621,502 S | 8/2010 | Downs |
| D630,317 S | 1/2011 | Wung |
| D636,894 S | 4/2011 | Tomes et al. |
| D638,137 S | 5/2011 | Gross et al. |
| D638,940 S | 5/2011 | Palmer et al. |

(56) References Cited

U.S. PATENT DOCUMENTS

| | | | |
|---|---|---|---|
| RE42,507 E | 6/2011 | Wilkinson et al. | |
| D648,852 S | 11/2011 | Shi | |
| D650,912 S | 12/2011 | Tomes et al. | |
| 8,114,103 B2 | 2/2012 | Rasco | |
| 8,156,653 B2 | 4/2012 | Austria | |
| 8,205,340 B2 | 6/2012 | Austria et al. | |
| D662,989 S | 7/2012 | Vulgamott et al. | |
| D676,146 S | 2/2013 | Austria | |
| D676,573 S | 2/2013 | Austria | |
| 8,372,503 B2 | 2/2013 | Austria et al. | |
| D683,407 S | 5/2013 | Austria | |
| D683,452 S | 5/2013 | Davies et al. | |
| D703,626 S | 4/2014 | Hermansen | |
| D710,497 S | 8/2014 | Pham et al. | |
| D712,062 S | 8/2014 | Austria | |
| D712,063 S | 8/2014 | Austria | |
| D712,064 S | 8/2014 | Austria | |
| D713,958 S | 9/2014 | Srinivasan et al. | |
| 8,898,910 B2 | 12/2014 | Ichiyanagi et al. | |
| 8,931,181 B2 | 1/2015 | Milton et al. | |
| 9,113,946 B2 | 8/2015 | Hajgato et al. | |
| 9,622,773 B2 * | 4/2017 | Austria | A61B 17/3213 |
| 2004/0186496 A1 | 9/2004 | Sandel et al. | |
| 2004/0243161 A1 | 12/2004 | Kanodia et al. | |
| 2005/0065541 A1 | 3/2005 | Abidin et al. | |
| 2005/0204932 A1 | 9/2005 | Tingley | |
| 2005/0223640 A1 | 10/2005 | Hall et al. | |
| 2006/0027104 A1 | 2/2006 | Perez, Jr. | |
| 2006/0041267 A1 | 2/2006 | Henry | |
| 2006/0100650 A1 | 5/2006 | Kiehne | |
| 2006/0212058 A1 | 9/2006 | Djordjevic et al. | |
| 2007/0039844 A1 | 2/2007 | Zyzelewski et al. | |
| 2007/0039845 A1 | 2/2007 | Kaforey et al. | |
| 2007/0255298 A1 | 4/2007 | Djordjevic et al. | |
| 2007/0265651 A1 | 11/2007 | Yi et al. | |
| 2008/0173187 A1 | 7/2008 | Baker | |
| 2008/0272023 A1 | 11/2008 | McCormick et al. | |
| 2009/0192538 A1 | 7/2009 | Sandel et al. | |
| 2009/0267717 A1 | 10/2009 | Baskett | |
| 2010/0023040 A1 * | 1/2010 | Austria | A61B 17/3213 606/167 |
| 2010/0137894 A1 | 6/2010 | Ueno et al. | |
| 2010/0228274 A1 | 9/2010 | Baid | |
| 2010/0268258 A1 | 10/2010 | Maxwell | |
| 2012/0245610 A1 | 9/2012 | Hajgato et al. | |
| 2012/0311869 A1 | 12/2012 | Ichiyanagi et al. | |
| 2013/0079804 A1 | 3/2013 | Milton et al. | |
| 2013/0245656 A1 | 9/2013 | Austria | |
| 2015/0201957 A1 | 7/2015 | Shi | |
| 2015/0250492 A1 | 9/2015 | Austria | |
| 2016/0095614 A1 | 4/2016 | Austria | |
| 2017/0181763 A1 * | 6/2017 | Austria | A61B 17/3213 |

FOREIGN PATENT DOCUMENTS

| | | |
|---|---|---|
| GB | 2464751 A | 5/2010 |
| JP | 3026909 B2 | 3/2000 |
| JP | 3126664 B2 | 1/2001 |
| JP | 2002177291 A | 6/2002 |
| JP | 2006340857 A | 12/2006 |
| JP | 5390694 B2 | 1/2014 |
| WO | 9424020 A1 | 10/1994 |
| WO | 2008132762 A1 | 11/2008 |
| WO | 2011108099 A1 | 9/2011 |
| WO | 2012002910 A1 | 1/2012 |

OTHER PUBLICATIONS

Smeak, Daniel et al., Core Surgical Skills: Basic Instrument Use, Texas A&M University School of Veterinary medicine and Biomedical Sciences, 2011, pp. 1-9.

Swann-Morton, Surgical Blade removal by Swann-Morton, date unknown, 2 pages.

Trademark Medical, Personal Protective Equipment & Sharps Safety Products: Scalpel Safety, 2010, 2 pages.

The Official Journal of the Anethesia Patient Safety Foundation, APSF Hosts Medication Safety Conference, vol. 25, No. 1, 1-20, 2010, 7 pages.

ADV Medical, Needle Counters Selection, date unknown, 2 pages.

Southmedic, Introducing . . . The only safety scalpel that fits your favorite handle, Safety Cabo, date unkown, 2 pages.

Tyco Healthcare Group LP, Devon* Needle Counters, 2003, 2 pages.

Xodus Medical, Needle Counter and Sharps Disposal Systems, date unknown, 4 pages.

* cited by examiner

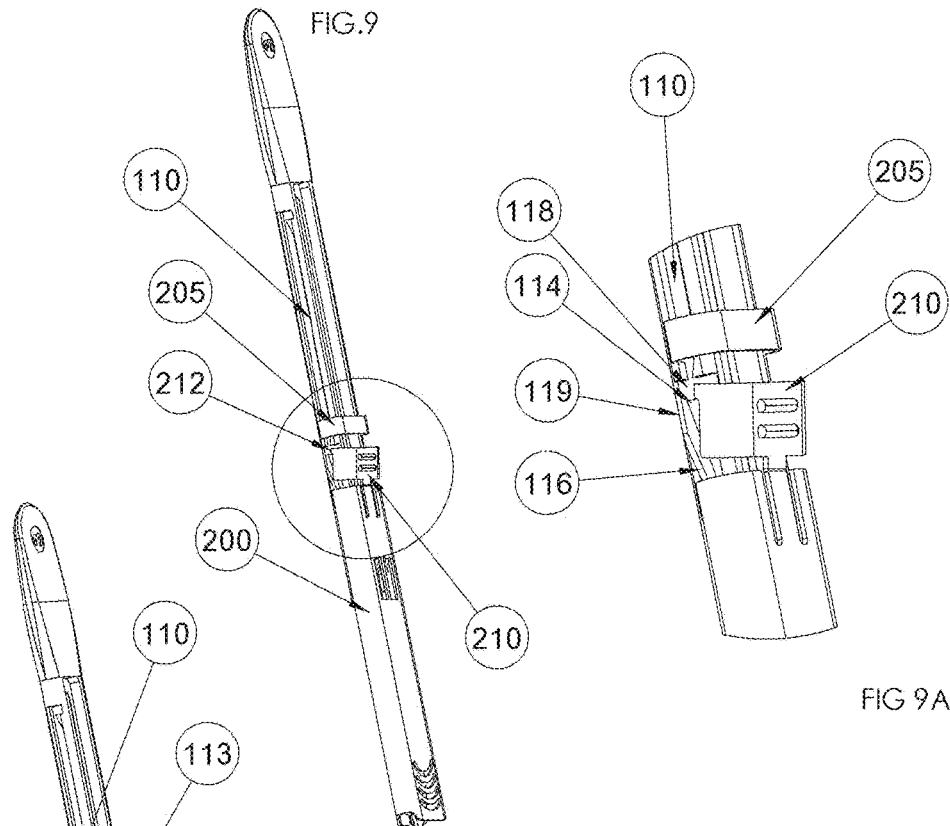
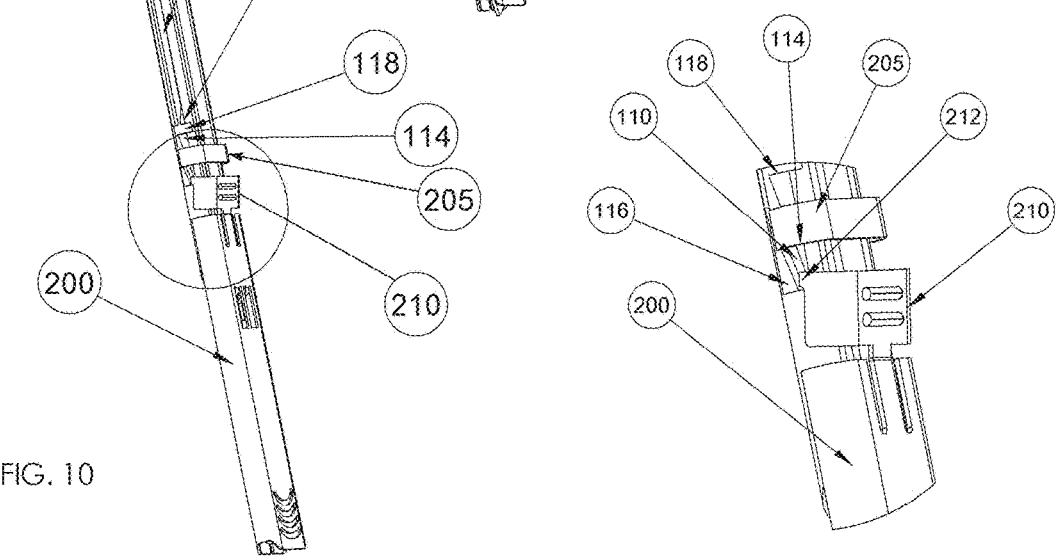

SIDE ACTIVATED SAFETY SCALPEL FOR LEFT AND RIGHT HAND USERS WITH BLADE REMOVAL SYSTEM

CROSS-REFERENCE TO RELATED APPLICATIONS

The present application is a continuation of pending U.S. patent application Ser. No. 13/802,522, filed Mar. 13, 2013, entitled "Side Activated Safety Scalpel for Left and Right Hand Users with Blade Removal System," now U.S. Pat. No. 9,622,773, which claims benefit of provisional application No. 61/685,480, filed Mar. 19, 2012, entitled "Side Activated Safety Scalpel for Left and Right Hand Users with Blade Removal System," the entire disclosures of which are hereby incorporated herein by reference.

BACKGROUND OF THE INVENTION

This invention covers the field of application where users are needing protection from accidental punctures from scalpel blades during the use and storage of surgical scalpels. More importantly, this invention allows the user of the device to be either left or right handed while still being able to use the device with the controlling mechanism located next to the user's thumb. The user of this invention also is able to ascertain the position of the shield through tactile sensory perception as well as having the safety of knowing that removal of the blade is only accomplished by a secondary ejectment location of the shield which is not part of the normal operation of the shield.

Each year many users accidentally slice or puncture themselves with sharp instruments either during use, during transfer from one person to another or from inadvertent misplacement of sharps in potentially dangerous locations. This is especially dangerous in the medical arena, as potentially fatal diseases can be spread through accidental contact with sharps. Emergency Rooms are battlegrounds compared to the operating rooms where quick action amongst many people is required to save lives. Sharp protection is a must and must be easy to operate. Prior art is replete with many different styles of devices that act to cover sharp blades.

There are 4 main types of prior art that exist to prevent users from accidental contact with sharp blades. The 4 areas involve devices where 1) the sharp is retracted into the body of the device; 2) where the device is a disposable or single use application, where the entire sharp with the handle is not reused; 3) a device that moves in a non-linear fashion to cover the blade while it is not in use; and 4) those devices which remove a detachable blade from the handle of the device. Only the fourth type of devices is applicable to this invention as the shield slides in a linear path along the handle.

The fourth arena of the prior art involves the use of devices whereby the sharp is attached to and then removed from the handle. In one group, there are those devices where the sharp is directly attached to the handle and another group contains devices where the sharp is placed into a cartridge which is then placed upon the handle. Both groups involve handling of the sharp prior to its inclusion into some protective cover, increasing the chance of accidental puncture. In the first group, Herbert et al in U.S. Pat. No. 5,868,771 issued on Feb. 9, 1999, Newman et al in U.S. Pat. No. 6,626,925 issued on Sep. 30, 2003 and van der Westhuizen et al in U.S. Pat. No. 5,330,494 disclose the procedure of attaching the sharp to the handle and then attaching a sliding blade guard. Once the sharp is used, the blade can be removed along with the guard. Herbert uses existing style surgical handles, while van der Westhuizen and Newman use a unique handle that is modified at the distal end of the handle nearest the sharp, to receive the guard. Both devices require the user to load the sharps device onto the handle, requiring the unguarded sharp to be handled by those that the device is designed to protect, and often those people are wearing gloves which will reduce tactile feel. In a different approach disclosed by Noack in U.S. Pat. No. 5,312,429 issued on May 17, 1994, a unique blade with an opposed tang is removed by sliding the blade release element when the element is slid down the handle toward the sharp. This is a two handed operation involving two separate pieces. In the sliding of the element, if one's hand slips from the element it would be certainly cut by the exposed blade. Also the blade is without direction or restraint when released from its location on the handle. It could fly anywhere in the operating room as there is tension built up between the tang of the blade and the rest of the blade that was forced over the post on the handle.

Cartridge types highlighted by U.S. Pat. No. 7,207,999 to Griffin et al issued on Apr. 24, 2007, show the use of a cartridge that contains the blade for the scalpel. The cartridge doubles as a shield when it is retracted over the handle after the attachment of the blade to the tang of the handle. Each cartridge is unique to a particular style of blade and requires a two handed operation to remove and attach the blade. This extra cartridge material creates costly waste. It is also against current disposal regulations to mix plastics with metal sharps containers as they require different disposal techniques. U.S. Pat. No. 7,172,611 issued to Harding et al on Feb. 6, 2007 shows another cartridge but this one is required to use a special blade with "non-arcuate" holes which increase the cost and decreases its effectiveness to be used with a broad range of access. All cartridge style scalpels use the removal of the cartridge that contains the blade as the means for blade removal. Though safe, these devices are limited by needing unique cartridges to hold the wide variety of blades available.

Another adaptation of this concept, which is closer to the current invention, is found in the series of patents from Jolly et al, U.S. Pat. Nos. 5,827,309; 5,752,968 and 5,792,162 issued Oct. 27, 1998, May 19, 1998 and Aug. 11, 1998 respectively. These Jolly patents show a blade remover which first removes the tang of the blade from the post into a notch on the sliding guard. The '968 Patent discloses that "guard 30 can be advanced distally to force blade 50 from blade carrier". The built in stresses mentioned above are now increased with a forcible removal of the blade with the sliding guard, increasing the chance for the blade to be misdirected about the operating room. In the second group, Gharibian in U.S. Pat. No. 5,527,329 issued on Jun. 18, 1996 and Cohn et al in U.S. Pat. No. 5,938,676 issued on Aug. 17, 1999 disclose the use of a cartridge system whereby the sharp is placed into a cartridge which is then encased by a guard prior to its placement onto the handle. This operation is safer as the sharp is guarded during assembly but creates a situation as each discloses a unique handle designed to receive the cartridges and shields. Cohn et al in U.S. Pat. No. 5,941,892 issued on Aug. 24, 1999 combines prior art by incorporating the cartridge concept that is "removably retained within the cavity" in the handle. This is a safe alternative but uses unique handles. All of the prior art in this section requires the use of two hands to safely operate the device which is at odds with current FDA compliance rules.

In the last arena of prior art, a guard is placed around a stationary blade. There is nothing unique about the concept, and its application can be seen from the simple to the complex. Applications of a more complex nature are found in Abidin et al in U.S. Pat. No. 5,662,669 issued on Sep. 2, 1997 and U.S. Pat. No. 5,569,281 issued on Oct. 29, 1996, Jolly et al in U.S. Pat. No. 5,741,289 issued on Apr. 21, 1998, Matwijcow in U.S. Pat. No. 5,207,696 and Dolgin et al in U.S. Pat. No. 5,071,426 issued on Dec. 10, 1991. Matwijcow discloses a rack and pinion system for movement of the guard over the blade which causes a reverse sequence of logic, as the user needs to pull back to move the guard forward. This could be confusing in the fast paced operating room where several different types of devices might be used at once. Dolgin also uses a "linkage system" to extend the blade guard "over a substantially greater distance than the distance which the surgeon's fingers move in operating the actuating mechanism". This is an unnecessarily complex and expensive concept using unique handles which require manual loading of the blades onto the handle. Jolly provides for both linear actuation of the guard along with a rotational movement of the guard and blade away from the handle for cleaning purposes. This device is complex and expensive to manufacture and use. The Abidin '281 patent discloses a guard which "comprises an inverted U-shaped channel member telescopically mounted within the hollow handle for sliding movement therein". It is held in position by an exposed pin which would be in the way of the surgeon's hands and could be accidentally triggered to move at the improper time. This device is also not usable with currently used scalpels and it requires a unique handle. Abidin '669 is another internally guided blade guard with a unique handle. But this patent also discloses in column 10 line 11, that it does not work with conventional scalpel blades. '669 does combine a blade guard and a blade ejector, but FIG. 36 details the need for two handed operation to remove the blade. FIG. 45 and FIG. 48 show that the blade is not restrained after it is removed from the handle, and as described above, there is a considerable amount of tension on the blade. The disclosure details the added tension as the guard actually pushes the blade off of the post upon which it is attached. There is nothing to restrain the loose blade. An unrestrained blade could fly off anywhere in the operating room and this is not a safe method of removal. '669 also discloses in FIG. 32 the complicated way of attaching the blade with two small pins, which would be very difficult with gloved hands in a hurried operating room. FIG. 130 of '669 shows the user sliding the guard forward using their forefinger, which would present an obvious problem should the guard become slippery due to bodily fluids, and the user's finger slips from the guard onto the exposed blade.

The inventor of this current invention has his own prior art in the field of scalpels that have a blade that is attached/detached from a handle, but differ substantially from the current invention. U.S. Pat. No. 8,156,653 issued on Apr. 17, 2012 to Austria, discloses a top rail mounted scalpel with three basic segments. That invention requires the use of two hands in order to eject the blade and the blade becomes trapped in the shield, requiring the use of another action by the user to get rid of the sharps blade, which is not desirable as well as having an impediment that all of the existing prior art possesses. The inability to be ambidextrous, allowing for left handed and right handed users to operate and to be trained upon one instrument in the same manner, while enjoying all of the advantages of the "right" handed version.

There is a need to preclude the problems associated with the prior art and the current state of technology in this field. It would be preferable to produce a device that would provide current users with a device that would improve upon some of the shortcomings of the prior art. Industry has set standards for their equipment and it would be desirable to have a device that fits their standard equipment, rather than adapt to new equipment. Sharps users, especially surgeons, are used to the weight, balance, fit, form and feel of their tools of the trade, and are reticent to change. It is well practiced in the medical field, that metal sharps handles are used because they possess a certain weight and balance that plastic handles have a hard time replicating. Industry needs to adapt protections to currently used sharps, as new devices are usually met with skepticism and doubt, and are thus not used. Industry does not want to carry duplicative inventories of many similar products because they do not work with one another.

It is also important to recognize that though only 7% of the population are considered left-handed, over 15% of all surgeons are left-handed according to the British Medical Journal in 2005, which found that left-handed surgeons are forced to use right handed devices causing a greater incident of accidental punctures from sharps. Left handed surgeons should be able to use devices designed for left-handed surgeons while accommodating the number of devices that a hospital must have in its inventory. A device that is capable of use by right or left handed surgeons reduces the amount of inventory that must be carried by the surgical institution.

It would be desirable to have a new device made in such a manner that it could have multiple users, and could be reusable. It would be desirable to have the device made of autoclavable plastic or metal and designed so that it will not have any hidden recesses or other cavities that would trap harmful bacteria precluding the chance that it could be autoclavable. It would be desirable and advantageous to possess a blade removing apparatus which is designed not to interfere with a user's single handed operation of the device while insuring that accidental removal of the blade is eliminated.

It would be desirable to have a scalpel to be able to easily remove and change blades during surgical procedures, whereby one handle is capable of receiving multiple sizes and shapes of blades.

These and other features, advantages, and objects of the present invention will be further understood and appreciated by those skilled in the art by reference to the following specification, claims, and appended drawings.

SUMMARY OF THE INVENTION

Accordingly, it is the goal of this invention to create a sharps protection device that has the aforementioned characteristics of simplicity, protection, adaptability to current uses and safety. It is an object of this invention to create a device that will protect both the user of the sharp as well as the person who comes in accidental contact with misplaced sharps, and for the person to whom the sharp is transferred.

It is an object of this invention to create a device that is operable with a single hand and allows for the user to be either left or right handed to operate the device. The user must be able to retract or extend the sharps guard and be able to remove the sharp from the handle if that option is available to the user with the particular sharp.

It is an object of this invention to create a device that does not interfere with the normal operation of the scalpel and that does not substantially change the feel of the scalpel. It is an object of this invention to create a device whose design allows for the modification of said design altering the weight and balance characteristics while maintaining overall design allowing for interchangeability.

It is an object of this invention to create a device that is rapidly interchangeable between a wide range of sharp's blades of varying devices from different manufacturers. The device must be simple to use and maintain. Users must be able to disassemble, clean, and reassemble in a matter of moments, while using gloved hands with reduced tactile feel. The device must have no small or intricate parts which would preclude the quick assembly of the device or that would foul or catch on the gloved hands of the surgical team.

It is an object of this invention to create a device which adapts to current state of the art devices, reducing the need for training, evaluating and maintaining multiple inventories of devices and sharps. It is an object of this invention that industry standard blades, which are accepted onto a wide range of currently existing handles, are to be used without modification to the blade or handle.

It is an object of this invention to create a device which has positive stops, including tactual and auditory signals, indicating the relative position of the guard, either in retraction or extension of the surgical safety scalpel.

It is an object of this invention to create a device that does not involve placing of the protective device over the sharp in such a manner that actually increases the likelihood of accidental contact with the sharp. The user should be able to use the device immediately "out of the box" without having to add guarding or assemble cartridges prior to safe use.

It is an object of this invention to create a device that will provide for safe removal of the sharp from the surgical safety scalpel while using only a single hand for the operation. It is a further object of this invention to have the sharp blade covered during the time the user's hands are ejecting the blade, thereby reducing the chance for accidental puncture and to restrict the possibility of having the blade ejected into the surgical arena.

It would be desirable to create a device which is autoclavable or sterilizable in any accepted means, and is cleanable without disassembly, the device being absent of internal voids, sharp corners, chambers or holes which trap unsanitary material precluding the ability to easily clean and sanitize the device through autoclaving or other means and reuse of the device. The use of autoclavable or autoclaving in this specification is not a limiting factor but rather a general statement of the process of sterilizing and/or cleaning the device, through whatever means that are currently accessible and acceptable by the industry.

BRIEF DESCRIPTION OF THE DRAWINGS

FIG. 1A is a detailed view of the rear portion of the invention detailing the shield's rendition device;

FIG. 9 is a frontal left side oblique view of the shield in the closed position;

FIG. 9A is a detailed view of the retention portion of the shield in the closed position;

FIG. 10 is a left side frontal oblique view of the shield in the ejectment position;

FIG. 10A is a detailed view of the retention portion of the shield in the ejectment position;

DETAILED DESCRIPTION

Figure 1:
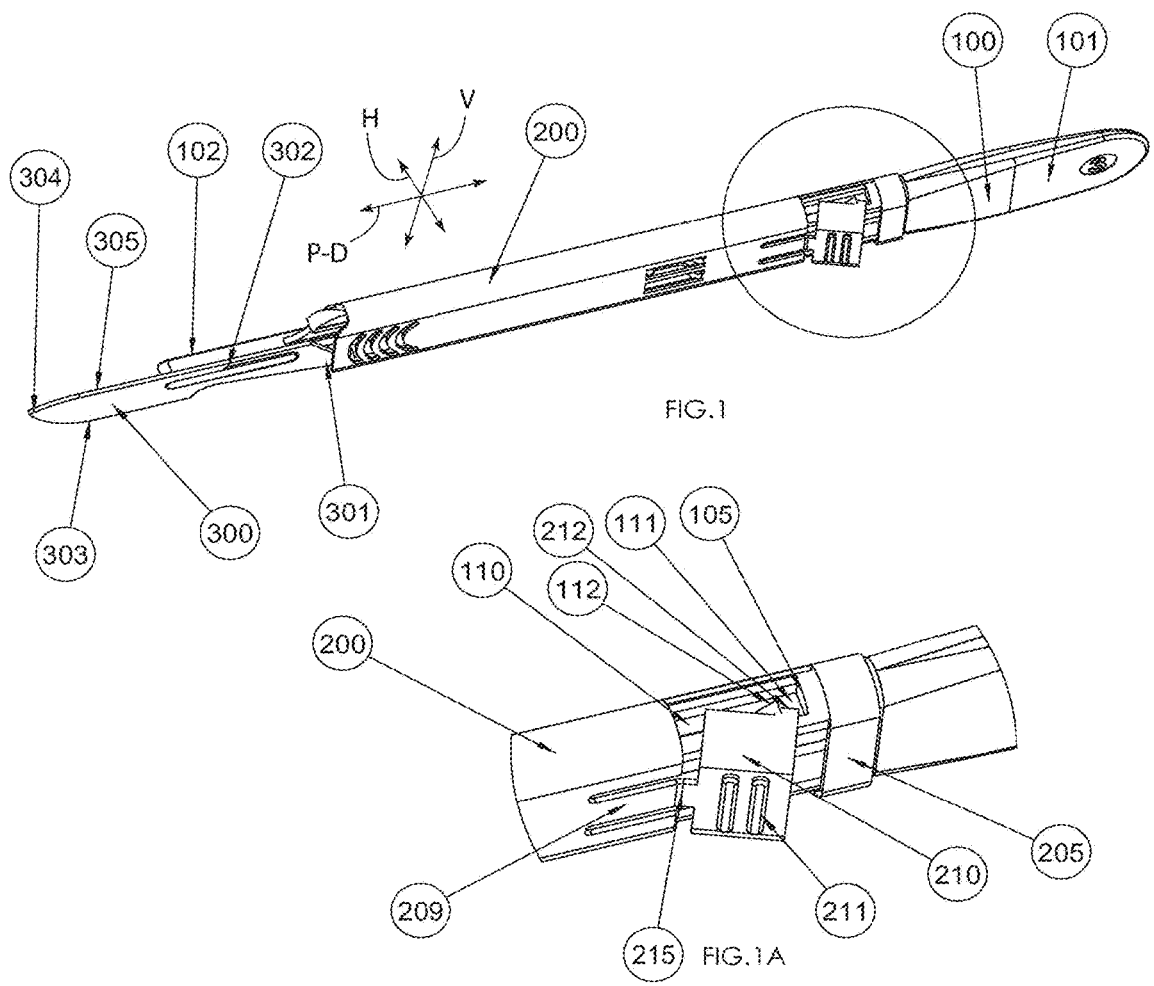
FIG. 1 is a left oblique position with the shield in the open position.

This invention as disclosed in the drawings has the principal use in the surgical environment but there exists no limiting language to prevent this invention to be practiced in other fields of use. The invention consists of three main elements, a handle, that holds the sharps blade, a shield that slides upon the handle, and having the shield also capable of removing the blade from the handle. This invention is a sharps device, such as a knife, scalpel or box opener, with a detachable shielding means which is capable of removing said sharp from said device.

Figure 4:
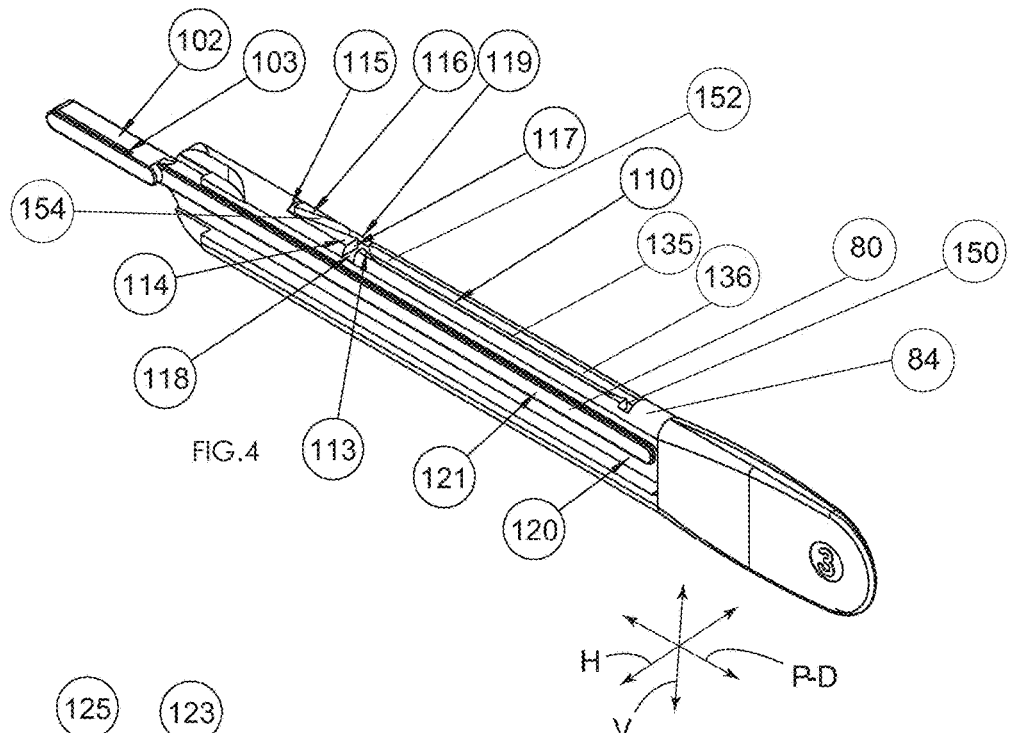
FIG. 4 is a left side rearward oblique view of the handle portion.

In FIG. 1, the invention is shown from a frontal left side view. Handle 100 has a distal tapered butt end 101 and a proximal end which contains sharps mounting post 102 as seen in FIG. 4. Handle 100 is basically rectangular in shape with two vertical (long) walls (inner vertical (long) face 80 and outer vertical (long) face 82, which extend in the vertical direction V and the proximal-distal direction P-D, as shown in FIG. 1) and two horizontal (short) surfaces (upper horizontal (short) surface 84 and lower horizontal (short) surface 86, which extend in the horizontal direction H and the proximal-distal direction P-D) conjoining the vertical walls 80,82. Though the shape is not critical to the success of the invention, it conforms to the feel and balance required by surgeons in their medical instruments. Channel 110 is located along at least one of the horizontal surfaces of the handle. It is shown in this invention to be on the upper horizontal surface but nothing prevents the channel to be in the lower horizontal surface with the associated shield interfaces located on the lower side as well or both surfaces. FIG. 1 shows shield 200 located in the rearward open position, exposing the sharp 300.

Sharp 300 having a cutting edge 303 which is opposite of the dull edge 305, sharp 300 having a vertical orientation basically parallel to the vertical faces of the handle 100.

Sharp 300 has a pointed distal end 304 and a proximal end containing the tang 301 of the blade. The blade 300 is mounted to handle 100 through an integral mounting feature 302 which interfaces with the sharps mounting groove 103. This invention is designed to accept industry standard surgical blades. FIG. 1A is a detailed view of the shield and handle interface when the shield is in the rearward or open position.

Figure 8:
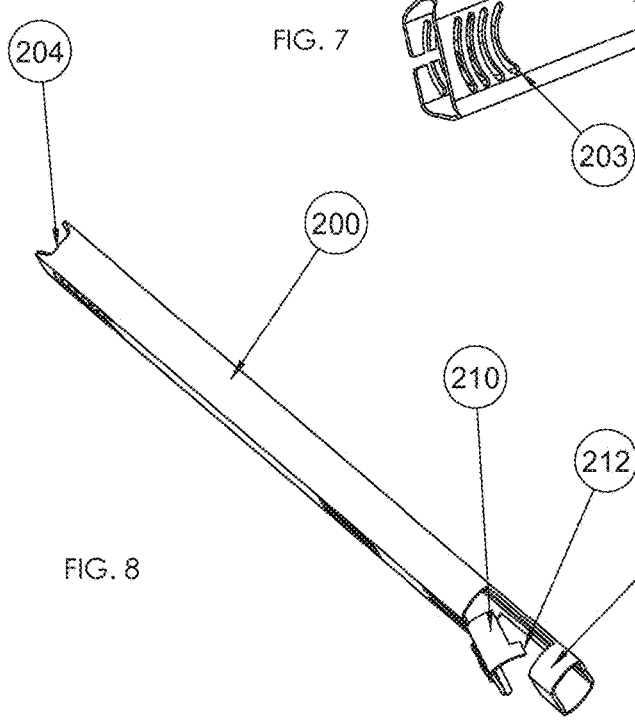
FIG. 8 is an upper side oblique view of the shield portion.

Shield 200 contains a side mounted button 210 where said button is mounted on the interior side of the device whereby it is accessible to the thumb of the user. Button 210 is outwardly biased due to the bias of flange 215 which flexes through flexor 209 which is integral to shield 200. The rear portion 205 of shield 200 is located behind the button area providing stability to the rear portion of the shield. The shape of rear portion 205 is designed so as to provide a close fit between the shield and the tapered butt end 101 as reasonable engineering tolerances will allow. The channel 110 includes a rearward shield open segment 150 and a forward closed shield segment 152 separated by segment 135 and a frontal ejectment segment 154. Each segment 150, 152, and 154 is generally defined by an inclined segment guide (ramp) 112, a positive tactile feel gutter (detent) 111, and a terminating segment wall 105. Also shown in FIG. 1A is the rear gutter (detent) 111 which is formed at the end of channel 110 after the button rides over rear portion inclined segment guide (ramp) 112. The user, as the shield transits through the channel 110 out of segment 135 will feel the button move inwardly, as guidance pin 212, as highlighted in FIG. 8, which rides in channel 110, approaches guide 112 and moves over guide 112, prior to snapping into rear gutter (detent) 111 terminating against rear termination wall 105. This tactile feel tells the user that the rearward travel is terminated and the gutter (detent) prevents accidental forward movement of the shield without deliberate user interaction to move the shield forward. It should be noted that the gutters (detents) are basically rectangular in nature with straight sides and bottoms. Button 210 has anti-slip feature 211, here shown as two vertical detents, which aid the user in finding the button through gloves and prevents accidental slippage of the user's thumb from the button during use. Alternate forms of anti-slip designs are available that can serve the same purpose or function.

Figure 2:
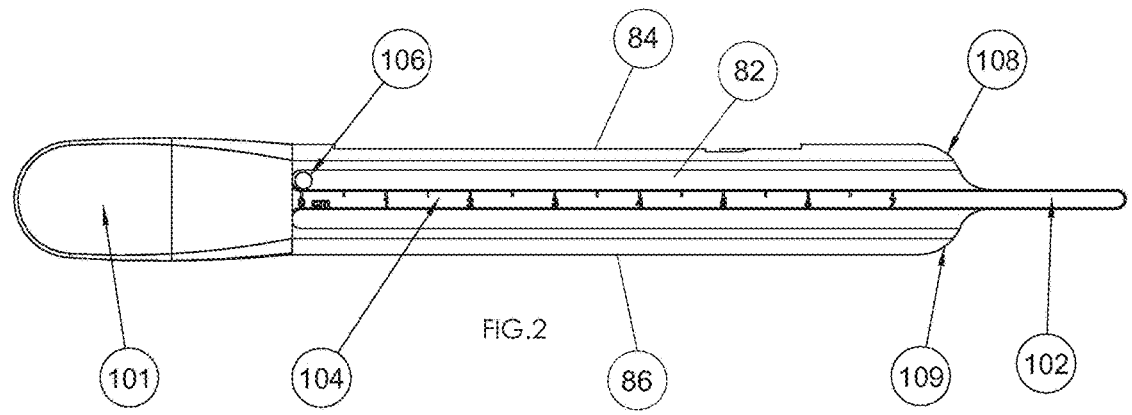
FIG. 2 is a right side rearward oblique view of the handle portion.
Figure 3:
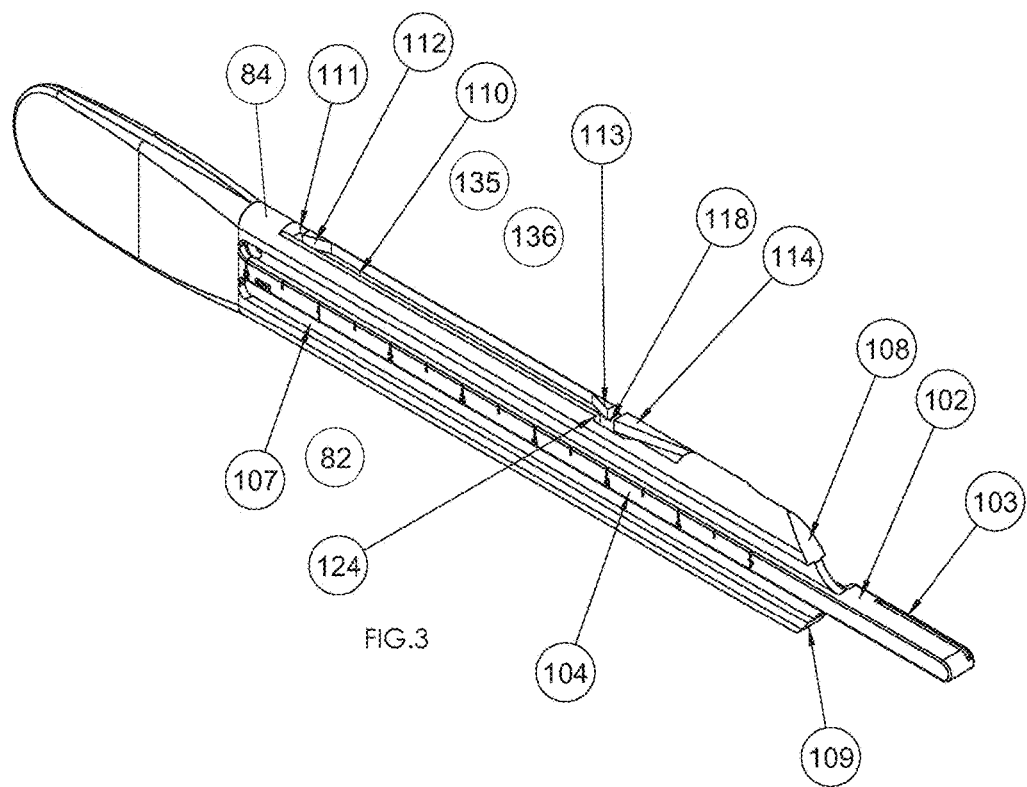
FIG. 3 is a right side frontal oblique view detailing the retention channel of the handle portion.

FIG. 2 shows the right side of the handle which shows optional ruler 104 which can be incorporated into this right side of the handle. FIG. 2 also highlights the radiused lead-in frontal edges. Upper frontal edge 108 and lower frontal edge 109 are similar in construction and shape and are designed to accommodate the attachment of sharp 300 in either an upward or downward orientation while attached to the mounting post 102 of the handle. Steam hole 106 is present to allow for passage of steam from one side of the handle to the other. Steam slot 107, shown in FIG. 3, is recessed in order to facilitate the flow of steam during autoclaving and the depth of the slot is also used as a weighing method, where the amount of material relieved from the handle directly affects the weight and the weighting characteristics of the handle to the preference of the user. FIG. 3 is an upper view highlighting channel 110. Forward inclined segment guide (ramp) 113 is similar to the shape and function of rearward guide 112. The user's forward progress of the shield is terminated against forward termination wall 117 and the guidance pin 212 rides over guide 113 and naturally falls into forward gutter (detent) 118, trapping the shield in the forward or closed position.

Figure 5:
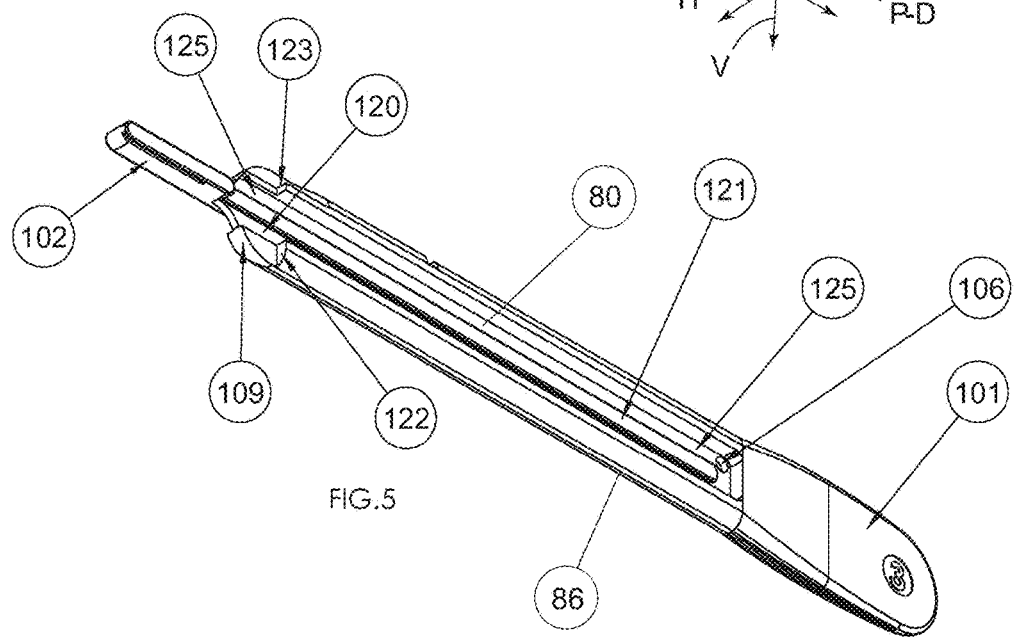
FIG. 5 is a left side frontal oblique view detailing the bottom portion of the handle portion.

Ejectment inclined guide (ramp) 114 is shown in FIG. 3 and FIG. 4. The height (in horizontal direction H away from outer wall 136) of the incline is at least twice that of the other two guides, 112 and 113. This increased height prevents accidental dislodgement of the shield in the forward position into the ejectment position. The user must consciously depress button 210 with a force at least twice that of the force necessary to transit the shield in the proximal-distal direction P-D from the open to the closed position. This extra force again designed to prevent accidental ejectment of the sharp from the handle. Once the user decides to eject the blade, the user depresses the button whereby pin 212 enters into ejectment bay 119, as shown in FIG. 4, riding down ejectment slope 116 terminating into forward ejectment gutter (detent) 115. At this point the blade has been removed, as discussed later, and the user retracts the shield, against wall 124 which defines the rear portion of ejectment bay 119. Forward gutter (detent) 118 is also used for shield attachment and detachment as well. For the user to remove the shield from the handle places the shield into the forward or closed positions with pin 212 in the forward gutter (detent) 118. The user then must retract the button, opposite of depressing the button, to allow for pin 21 2 to clear gutter (detent) 118 and the shield is then slid to forwardly. This is another unique safety feature, whereby the user must use a motion opposite of the normal operating motions of depressing the button in order to remove the shield, thereby reducing the risk of accidental removal of the shield, possibly exposing the sharp. Another unique safety feature is that the removal of the shield from the handle, necessitates the removal of the sharp from the handle as well, as discussed below, further reducing the risk of accidental contact with the exposed sharp. FIG. 5 shows the lower horizontal surface of handle 100 showing the upper and lower tang stops 123 and 122 respectively. FIG. 4 and FIG. 5 detail the weighting bar 121, which is designed to allow for specific user's preferences regarding the weighting characteristics of their preferred scalpel. The height of bar 121 and contouring of bar 121 can adjust the amount and location of the weighting of the handle 100.

Figure 6:
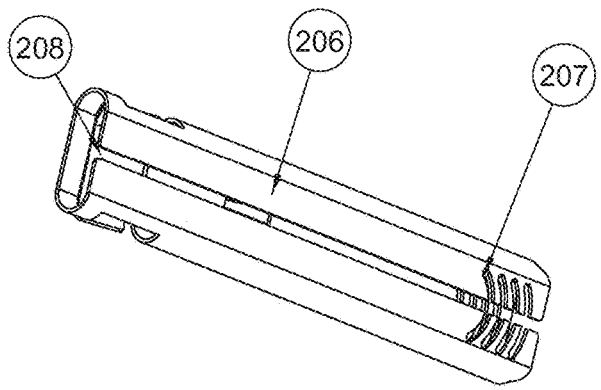
FIG. 6 is a right side oblique perspective of the shield portion.
Figure 7:
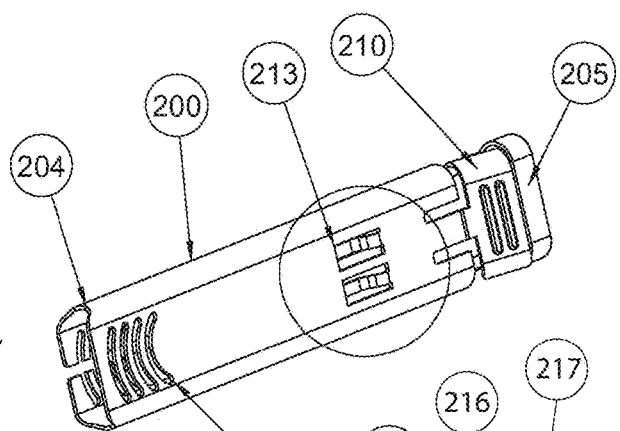
FIG. 7 is a left frontal oblique perspective of the shield portion.
Figure 7A:
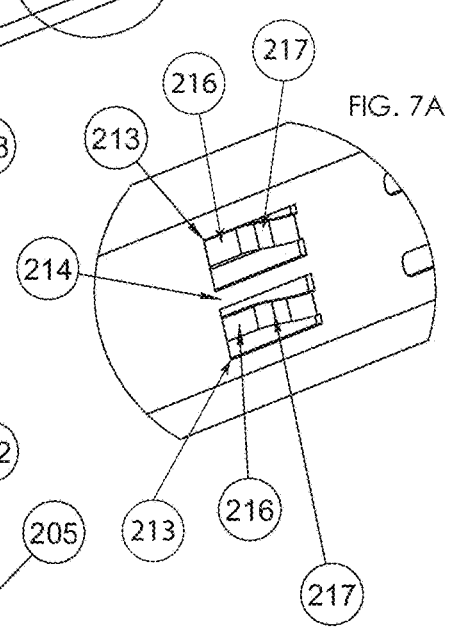
FIG. 7A is a detailed view of FIG. 7 showing the ejectment means on the left side of the shield.
Figure 10B:
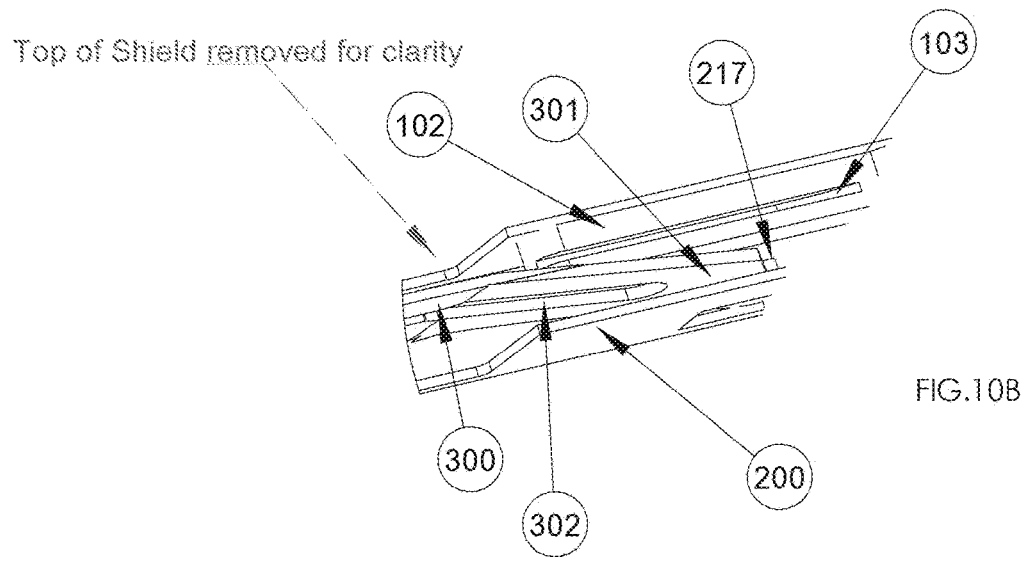
FIG. 10B is a detailed view during the ejectment process showing the ejectment means removed from the tang of the surgical blade from the handle portion, the top portion of the shield is removed for clarity purposes only.
Figure 10C:
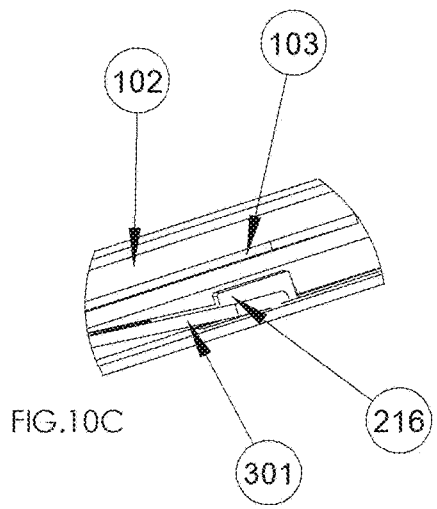
FIG. 10C is a detailed view during the ejectment process showing the ejectment means removed from the tang of the surgical blade from the handle portion, the top portion of the shield is removed for clarity purposes only.

FIG. 6 shows the rear or right side 206 of the exterior portion of shield 200 where it can be seen that the shield is not a solid cylindrical object. In the manufacturing process of forming the shield, which starts as a flat piece, mating area 208 is purposefully left as a gap to facilitate better steam movement during the autoclaving process and reduces the amount of material needed for the shield thereby reducing cost and weight. Rear steam slots 207 allow for entrance of steam should the shield be in the open position during the autoclaving process. The shape of rear steam slot 207 and front steams slots 203 are shown in this example as curved arcs, but any shape or design is available so long as the purpose of steam passage is accomplished. FIG. 7 shows the front view of shield 200 showing the concave entrance 204 which reduces the weight and materials needed while still giving protection over the critical middle part of the shield protecting users from the sharp distal end 304 of said sharp 300. FIG. 7A details the ejectors which are integral to shield 200, whereby the shield contains two ejector windows, separated by a solid bar 214 along the exterior portion of shield 200 which separates the two ejectors. The ejectors consist of a shovel nosed ejectment mechanism 216 which is held in an extended position in the horizontal direction H by extension 217 whereby mechanism 216 is substantially parallel to the interior face of shield 200. Each extension 217 holds each ejector mechanism 216 in a location whereby ejector mechanism 216 is coincident with tang 301 of blade 300 when the shield is in the closed position. In this invention, mechanism 216 is slightly under tang 301, but does not have to be in this location while the shield is in the closed position. It is only critical that the mechanism is capable of removing the tang 301 of blade 300 while the shield transits into the ejectment segment. Each ejector mechanism slides laterally within lower or upper ejector guide 120 and 125, as the shield transits between the open and closed position. FIG. 9 and detail FIG. 9A show the position of the shield at the closed position. At this point, though not shown, mechanism 216 is appurtenant to tang 301 of sharp 300. In FIG. 10 and detail FIG. 10A, the shield is moved into the ejectment segment whereby the blade is removed from the sharps mounting post 102, and freely falls into a sharps container guided by the interior portion of shield 200. FIG. 10C details the relationship between mechanism 216 and tang 301 as the shield is moved forward. FIG. 10B details sharp 300 as the integral mounting feature 302 as it is removed from mounting groove 103. As described herein, due to the increased amount of pressure needed to move the shield into the ejectment portion from the closed position, the fact that mechanism 216 is behind tang 301 at this position is not a detriment, as accidental dislodgement is not a consideration.

Figure 11:
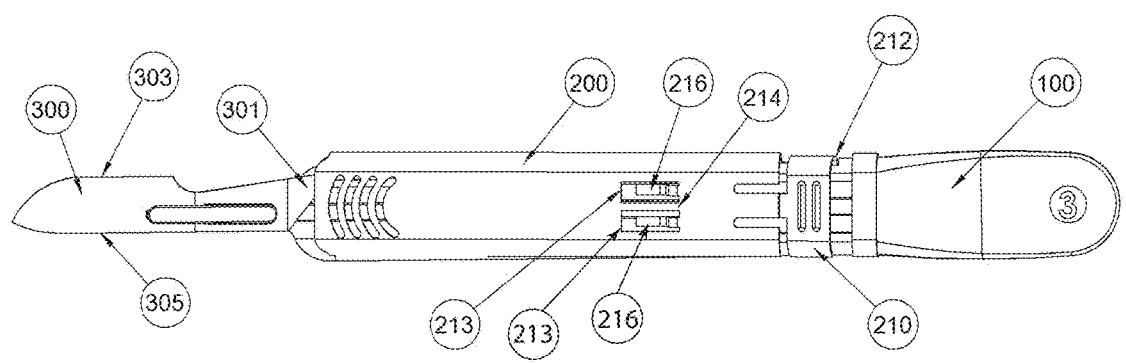
FIG. 11 is a left side planar view of the invention shown which highlights the uniqueness of the invention and also the ability to attach the scalpel blade in an inverse orientation which allows for use of the invention by left handed as well as right handed surgeons while maintaining the control portion of the shield location means towards the operator's thumb.
Figure 12:
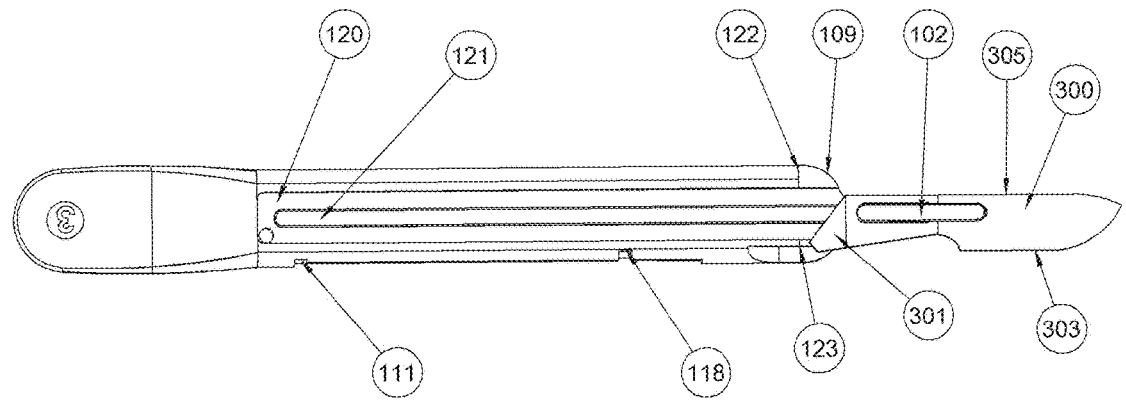
FIG. 12 is a right side planar view of the invention is shown which highlights the uniqueness of this invention in the ability to attach the scalpel blade in an inverse orientation which is shown by the scalpel number being upside down while the surgical blade's cutting surface is located downwardly. This view does not have the shield attached so that one can see the clearance of the tang of the blade.

Another unique feature of this invention is the ability to insert the sharp into either a cutting edge facing upwards or downwards as is more commonly done. Due to the shape and location of the tang stops 122 and 123, a sharps can be inserted in the normal cutting side down configuration as seen in FIG. 1 or a sharp can be inserted in an upward configuration such as seen in FIGS. 11 and 12, as one can see the orientation of the number "3" on the butt portion of the handle 100. Since there are many surgeons and sharps users that are left handed, it is a unique advantage of this invention to be ambidextrous. Currently left handed surgeons must use instruments designed for right handed users, where the controls are on the opposite side of the instrument and training on the instruments is aimed for right handed users, causing left handed users to either adapt to a right handed instrument or be forced to develop their own procedures. This invention allows for either a left handed or a right handed user to operate the device in the exact same manner, reducing the chances of errors due to improper handling and training on the use of the surgical device.

It can be appreciated by those appropriately skilled in the art that changes, modifications or embodiments can be made to this invention without departing from the spirit, principles, theories, ideas or conceptions that have been disclosed in the foregoing. It is herein recognized that the embodiments disclosed by this description of the best mode of practicing this invention, which will be hereafter described in their full breadth in the claims and equivalents thereof.

The invention claimed is:

1. A scalpel handle, comprising:
a body having a sharps mounting post disposed at and extending away from a first end of the body in a proximal-distal first direction; and
a shield retained on the body and slideable in the first direction between a retracted position and an ejectment position, the shield including a first ejectment arm extending inwardly from a portion of the shield in a second direction perpendicular to the first direction within an interior of the shield and defining a portion that is in a fixed position in the second direction and at least partially aligned with a portion of the sharps mounting post to pass the first end of the body and at least a rearward end of the sharps mounting post during movement of the shield into the ejectment position.

2. The scalpel handle of claim 1, wherein:
the sharps mounting post includes a mounting groove; and
the ejectment arm extends inwardly from the portion of the shield, the fixed position being such that the portion of the ejectment arm is behind the mounting groove in the first direction.

3. The scalpel handle of claim 1, wherein:
the first ejectment arm is positioned adjacent a first side of the sharps mounting post; and
the shield further includes a second ejectment arm positioned on a second side of the sharps mounting post opposite the mounting post in a third direction perpendicular to both the first and second directions and defining a portion that is in a fixed position in the second direction and at least partially aligned with the portion of the sharps mounting post.

4. The scalpel handle of claim 3, wherein:
the body defines first and second longitudinal ejector guides extending laterally inwardly from a side of the body adjacent the first and second ejectment arms and respectively positioned adjacent the first and second sides of the sharps mounting post; and
the first and second ejectment arms extend respectively into the first and second ejector guides.

5. The scalpel handle of claim 1, wherein:
the handle defines first and second opposite long surfaces, first and second opposite short surfaces extending between the long surfaces, and a first channel recessed into the first short surface, the first channel extending along a longitudinal axis of the handle; and
the shield includes a guidance pin extending into and traversing the channel during movement of the shield between the retracted position, in which the shield is positioned away from the sharps mounting post, and an extended position between the retracted position and the ejectment position, in which the shield extends over the sharps mounting post.

6. The scalpel handle of claim 5, wherein:
the shield further includes a positioning release button located on an exterior portion of the shield and connected to the exterior portion and outwardly-biased therefrom by a flange, the guidance pin being positioned on the positioning release button;
the channel includes a first detent positioned along a portion thereof and disposed toward the positioning release button; and
the guidance pin is engageable with the detent by an outward biasing thereof and is disengageable from the detent by inward movement of the positioning release button.

7. The scalpel handle of claim 6, wherein the detent is positioned within the channel such that the guidance pin engages the detent when the shield is in the extended position to restrict movement of the shield into either the ejectment position or the retracted position.

8. The scalpel handle of claim 7, wherein the detent is positioned within the channel such that the guidance pin engages the detent when the shield is in the retracted position to restrict movement of the shield toward the extended position.

9. The scalpel handle of claim 7, wherein the detent is adjacent an inwardly-extending ramp portion of the channel.

10. A scalpel handle, comprising:
a body defining first and second opposite long surfaces, first and second opposite short surfaces extending between the long surfaces, and a first channel recessed into the first short surface, the first channel extending along the handle in a proximal-distal first direction, the body including a sharps mounting post extending from a first end of the body and extending away from the channel in the first direction; and a shield retained on the body and slideable therealong in the first direction, the shield including:

a guidance pin extending into and traversing the channel during movement of the shield between a retracted position, in which the shield is positioned away from the sharps mounting post, and an extended position, in which the shield extends over the sharps mounting post; and a first ejectment arm extending inwardly from a portion of the shield in a second direction perpendicular to the first direction within an interior of the shield and defining a portion that is in a fixed position in the second direction at least partially aligned with a portion of the sharps mounting post to pass the first end of the body and at least a rearward end of the sharps mounting post during movement of the shield into an ejectment position.

11. The scalpel handle of claim 10, wherein:

the channel includes a first detent positioned along a portion thereof disposed toward the first long surface of the handle;

the shield further includes a positioning release button located on an exterior portion of the shield and connected to the exterior portion and outwardly-biased therefrom by a flange, the guidance pin being positioned on the positioning release button; and the detent extends toward the positioning release button such that the guidance pin is engageable with the detent by an outward biasing thereof and is disengageable from the detent by inward movement of the positioning release button.

12. The scalpel handle of claim 11, wherein the first detent is positioned within the channel such that the guidance pin engages the first detent when the shield is in the extended position to restrict movement of the shield into either the ejectment position or the retracted position.

13. The scalpel handle of claim 12, wherein the first detent is open on the first short surface of the handle to define a release channel traversable by the guidance pin by an outward force on the positioning release button beyond a natural outwardly-biased position thereof.

14. The scalpel handle of claim 12, wherein the first detent is flanked by first and second ramp portions inclined from portions of the channel disposed away from the detent to portions of the channel disposed adjacent the detent, the first detent being disposed toward the ejectment position and extending inwardly a first distance that is greater than a second distance through which the second ramp portion extends.

15. The scalpel handle of claim 11, wherein the first detent is positioned within the channel such that the guidance pin engages the detent when the shield is in the retracted position to restrict movement of the shield toward the extended position.

16. The scalpel handle of claim 15, wherein the detent is adjacent an inclined ramp portion of the channel.

17. The scalpel handle of claim 11, wherein:

the first detent is positioned within the channel such that the guidance pin engages the first detent when the shield is in the extended position to restrict movement of the shield into either the ejectment position or the retracted position; and a second detent is positioned within the channel such that the guidance pin engages the second detent when the shield is in the retracted position to restrict movement of the shield toward the extended position.

18. The scalpel handle of claim 10, wherein:

the body defines a first longitudinal ejector guide extending laterally inwardly from the first long surface of the body and positioned on a first vertical side of the sharps mounting post; and the first ejectment arm extends into the first ejector guide.

19. The scalpel handle of claim 18, wherein:

the shield further includes a second ejectment arm extending within an interior of the shield in a substantially fixed lateral position at least partially aligned with a portion of the sharps mounting post;

the body further defines a second longitudinal ejector guide extending laterally inwardly from the first long surface of the body and positioned on a second side of the sharps mounting post; and the second ejectment arm extends into the second ejector guide.

20. A scalpel handle, comprising:

a body including a sharps mounting post extending from a first end of the body in a proximal-distal first direction, the body defining first and second opposite long surfaces, first and second opposite short surfaces extending between the long surfaces, a detent recessed into the first short surface, and an ejectment channel portion extending from the detent toward the first end; and a shield retained on the body and slideable therealong in the first direction between an extended position and an ejectment position, the shield including:

a guidance pin positioned on an outwardly-biased positioning release button and engaging with the detent when the shield is in the extended position and being slideable into the ejectment channel portion upon inward deflection of the positioning release button; and a first ejectment arm extending inwardly from a portion of the shield in a second direction perpendicular to the first direction within an interior of the shield and defining a portion that is in a fixed position in the second direction and at least partially aligned with a portion of the sharps mounting post to pass at least a rearward portion of the sharps mounting post during movement of the shield from the extended position to the ejectment position.

* * * * *